(12) United States Patent
Shrivastav et al.

(10) Patent No.: US 8,372,013 B2
(45) Date of Patent: Feb. 12, 2013

(54) METHOD AND APPARATUS FOR DETERMINING A RESPIRATION PARAMETER IN A MEDICAL DEVICE

(75) Inventors: Maneesh Shrivastav, Blaine, MN (US); Yong K. Cho, Maple Grove, MN (US); Tommy D. Bennett, Shoreview, MN (US); Mark K. Erickson, Brooklyn Park, MN (US); Saul E. Greenhut, Aurora, CO (US); Karen J. Kleckner, New Brighton, MN (US); Charles P. Sperling, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1139 days.

(21) Appl. No.: 12/262,285

(22) Filed: Oct. 31, 2008

(65) Prior Publication Data

US 2010/0076322 A1   Mar. 25, 2010

Related U.S. Application Data

(60) Provisional application No. 61/098,282, filed on Sep. 19, 2008.

(51) Int. Cl.
*A61B 5/0205* (2006.01)
*A61B 5/08* (2006.01)

(52) U.S. Cl. ........................ 600/484; 600/529

(58) Field of Classification Search ........................ None
See application file for complete search history.

(56) References Cited

U.S. PATENT DOCUMENTS

| | | | |
|---|---|---|---|
| 4,803,997 A | 2/1989 | Bowman | |
| 5,003,976 A | 4/1991 | Alt | |
| 5,074,303 A | 12/1991 | Hauck | |
| 5,197,467 A | 3/1993 | Steinhaus et al. | |
| 5,273,034 A | 12/1993 | Nilsson | |
| 5,433,208 A | 7/1995 | Lundstrom | |
| 5,458,137 A | 10/1995 | Axe et al. | |
| 5,469,856 A | 11/1995 | Lundstrom | |
| 5,546,952 A | 8/1996 | Erickson | |

(Continued)

FOREIGN PATENT DOCUMENTS

| | | |
|---|---|---|
| DE | 4105457 A1 | 2/1991 |
| EP | 0029166 A1 | 5/1981 |

(Continued)

OTHER PUBLICATIONS

Monsine Karrakchou et al, "More Accurate Measurements using Mutual Wavelet Packets for Adaptive Filtering" IEEE Engineering in Medicine and Biology Magazine, IEEE Service Center, Pisacataway, NJ, US, vol. 14, No. 2, Mar. 1, 1995, pp. 179-185. Apr. 13, 2012.

(Continued)

*Primary Examiner* — Shanon A Foley
(74) *Attorney, Agent, or Firm* — Michael C. Soldner

(57) ABSTRACT

A method of determining a respiration parameter in a medical device in which pressure signals are sensed to generate corresponding sample points, and a breath detection threshold is continuously adjusted in response to the generated sample points to generate a current adjusted breath detection threshold. A current generated sample point is compared to the current adjusted breath detection threshold, and the continuous adjusting of the breath detection threshold is suspended and the breath detection threshold is equal to the most current adjusted breath detection threshold generated prior to the suspending in response to the comparing. A next sample point, generated subsequent to the suspending, is compared to the set breath detection threshold, and the respiration parameter is determined in response to the comparing of a next sample point to the set breath detection threshold.

19 Claims, 8 Drawing Sheets

U.S. PATENT DOCUMENTS

| | | | |
|---|---|---|---|
| 5,549,655 A | 8/1996 | Erickson | |
| 5,944,680 A | 8/1999 | Christopherson | |
| 5,974,340 A | 10/1999 | Kadhiresan | |
| 6,021,352 A | 2/2000 | Christopherson et al. | |
| 6,141,590 A | 10/2000 | Renirie et al. | |
| 6,459,929 B1 | 10/2002 | Hopper et al. | |
| 6,467,477 B1* | 10/2002 | Frank et al. | 128/203.23 |
| 6,471,658 B1 | 10/2002 | Daniels et al. | |
| 6,506,161 B2 | 1/2003 | Brockway et al. | |
| 6,641,542 B2 | 11/2003 | Cho | |
| 6,964,641 B2 | 11/2005 | Cho | |
| 7,100,607 B2 | 9/2006 | Zdrojkowski et al. | |
| 7,160,252 B2 | 1/2007 | Cho | |
| 7,186,220 B2 | 3/2007 | Stahmann et al. | |
| 7,200,440 B2 | 4/2007 | Kim et al. | |
| 7,314,451 B2 | 1/2008 | Halpenn et al. | |
| 2004/0111041 A1* | 6/2004 | Ni et al. | 600/544 |
| 2005/0085734 A1 | 4/2005 | Tehrani | |
| 2005/0148885 A1 | 7/2005 | Tweed et al. | |
| 2006/0064021 A1 | 3/2006 | Hefele | |
| 2006/0079793 A1 | 4/2006 | Mann et al. | |
| 2006/0094967 A1 | 5/2006 | Bennett et al. | |
| 2007/0118036 A1 | 5/2007 | Hersh et al. | |
| 2008/0034836 A1 | 2/2008 | Eigler et al. | |
| 2010/0076322 A1* | 3/2010 | Shrivastav et al. | 600/484 |

FOREIGN PATENT DOCUMENTS

| | | |
|---|---|---|
| EP | 0449401 | 10/1991 |
| EP | 1175919 | 1/2002 |
| WO | 9749455 | 12/1997 |
| WO | 0021438 | 4/2000 |
| WO | 0066215 | 11/2000 |
| WO | 0228460 | 11/2002 |

OTHER PUBLICATIONS

Xin Zhu et al , "Real-Time Monitoring of Respiration Rhythm and Pulse Rate During Sleep", IEEE Transactions on BioMedical Engineering, IEEEE Service Center, Piscataway, NJ, US, vol. 53, No. 12, Dec. 1, 2006, pp. 2553-2583.

Varanini et al, Adaptive Filtering of ECG Signal for Deriving Respiratory Activity, Computers in Cardiology 1990, Proceedings., Sep. 23-26 1990, pp. 621-624.

Marques De Sa et al., Diginal FIR Filtering for Removal of ECG Baseline Wander, Journal of Clinical Engineering, Jul.-Sep. 1982, pp. 235-40.

Sommo, Time-varying digial filtering of ECG baseline wander. Med & Biol Eng & Comut, 1993, vol. 31, pp. 503-08.

* cited by examiner

METHOD AND APPARATUS FOR DETERMINING A RESPIRATION PARAMETER IN A MEDICAL DEVICE

RELATED APPLICATION

The present application claims priority and other benefits from U.S. Provisional Patent Application Ser. No. 61/098,282, filed Sep. 19, 2008, entitled "PRESSURE DERIVED RESPIRATION MONITORING", incorporated herein by reference in its entirety.

CROSS-REFERENCE TO RELATED APPLICATIONS

Cross-reference is hereby made to the commonly assigned related U.S. application Ser. Nos. 12/261,300, entitled "METHOD AND APPARATUS FOR DETERMINING A RESPIRATION PARAMETER IN A MEDICAL DEVICE", to Shrivastav et al.; 12/262,277, entitled "FILTERING OF A PHYSIOLOGIC SIGNAL IN A MEDICAL DEVICE", to Cho et al.; 12/262,307, entitled "METHOD AND APPARATUS OF DETERMINING A RESPIRATION PARAMETER IN A MEDICAL DEVICE", to Cho et al.; 12/262,320, entitled "METHOD AND APPARATUS FOR DETERMINING RESPIRATORY EFFORT IN A MEDICAL DEVICE", to Cho et al., filed concurrently herewith and incorporated herein by reference in their entireties.

TECHNICAL FIELD

The invention relates generally to medical devices and, in particular, to a medical device system and method for filtering of a physiologic signal in a medical device.

BACKGROUND

Respiration monitoring is useful in diagnosing and managing pathological conditions. Respiratory rates can be measured and respiratory effort can be observed during clinical office visits but potentially important changes that occur outside of the clinical setting cannot be observed. Heart failure patients can experience dyspnea (labored breathing) upon exertion. As heart failure worsens, dyspnea can occur at relatively low levels of exertion, at rest and during certain postures. Heart failure patients can also experience disrupted breathing patterns such as Cheyne-Stokes breathing and sleep apnea. Episodes of disrupted breathing patterns are not easily captured during clinical office visits. Ambulatory monitoring of respiration is desirable for capturing useful diagnostic data and tracking a patient's disease state. Implantable devices used for chronic monitoring of patients are generally minimized in size to avoid patient discomfort. It is desirable to include respiration monitoring capabilities in an implantable monitoring device without substantially adding to the overall size and complexity of the device.

DETAILED DESCRIPTION

Figure 1:
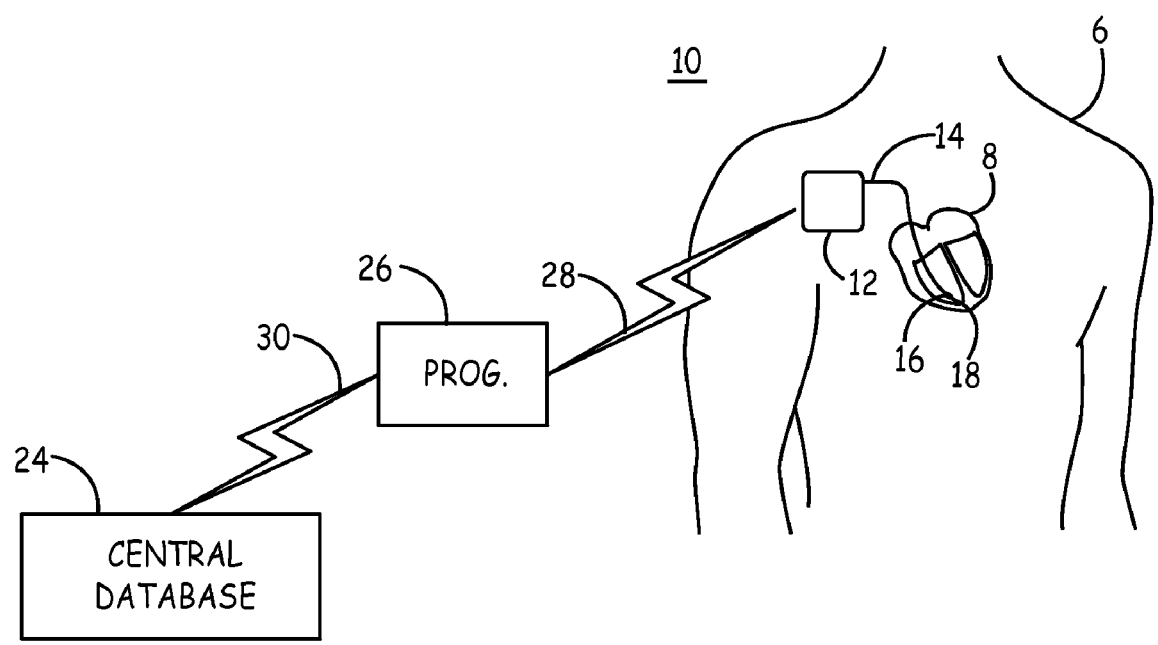
FIG. 1 is a schematic diagram of a patient monitoring system including an implantable medical device coupled to a lead positioned within a patient's heart.

In the following description, references are made to illustrative embodiments. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Various embodiments described herein utilize a pressure signal for deriving a respiration signal for respiration monitoring. As used herein, the term "pressure signal" includes any pressure signal measured within the body that includes a cardiac signal component and a respiration signal component. Such pressure signals include, for example, a pressure signal measured within a cardiac chamber, also referred to herein as an "intracardiac pressure signal". Intracardiac pressure signals may be measured in the right or left atrium or in the right or left ventricle. Pressure signals used for deriving a respiration signal as described herein can include pressure signals measured in any blood volume, including within a blood vessel. Pressure signals used for deriving a respiration signal can also include internal pressure signals measured within a tissue or body cavity, such as in the pericardial space, mediastinal space, intrapleural space or within the myocardial tissue, all of which pressure signals may include both a cardiac and respiratory component. It is noted that the relative contributions of the respiratory and cardiac components to both the amplitude and the frequency content of the pressure signal will vary depending on the sensing site.

It is further noted that a respiration signal derived from an internal pressure signal is not a direct measure of the volume of air moved in and out of the lungs during breathing. Under many circumstances, the amplitude changes of the pressure-derived respiration signal will provide a strong correlation to actual respiration volumes, i.e., the actual volume of air moving in and out of the lungs. This correlation, however, will depend on the airway resistance. For example, airway resistance may increase in obstructive sleep apnea, causing a decrease in the inspired air volume. Yet at the same time, the peak-to-peak amplitude of a pressure-derived respiration signal will likely increase. This increase reflects an increased respiratory effort made by the patient, i.e. increased work performed by the respiratory muscles to inhale, and does not correspond to an increase in the volume of inspired air. As such, a pressure-derived respiration signal is a good indicator of respiratory effort since the measured internal pressures will reflect the effort being made by the patient to breath. Changes in the pressure-derived respiration signal may or may not be accompanied by actual changes in respired air volume, depending on the airway properties.

In summary, the term "respiration signal" as used herein, referring to a signal derived from a pressure signal, can be considered a "respiratory effort signal." The negative-going signal peaks of the pressure-derived respiration signal are referred to herein as "peak inspiratory effort" since these peaks correspond to the patient's effort to inspire. The positive-going respiration signal peaks are referred to herein as "peak expiratory effort" since these positive going peaks correspond to the patient's effort to expire. The difference between a positive-going and negative going peak of the pressure-derived respiration signal can be determined as one measure of respiratory effort as will be described herein. However, it is recognized that the actual time point of maximum inspiratory effort and maximum expiratory effort as defined as actual work performed by the muscles involved in respiration may or may not coincide in time with the pressure-derived respiration signal peaks.

As will be described herein, the pressure-derived respiration signal, or "respiratory effort signal," is useful for detecting temporal features of respiration, for example the timing of inspiration and expiration phases and the respiration rate. Detection of such temporal features allows patterns of abnormal breathing to be detected. The pressure-derived respiration signal is also useful for determining a measure of respiratory effort as described above. The pressure-derived respiration signal may or may not be mathematically correlated to actual respired air volumes depending on individual circumstances.

The use of a pressure signal for deriving a respiration signal enables respiration monitoring to be incorporated in an implantable monitoring device that already includes a pressure sensor. For example, an implantable medical device that includes hemodynamic monitoring may include a pressure sensor positioned in a heart chamber or blood vessel. Respiration monitoring using a respiration-derived pressure signal may be incorporated in the hemodynamic monitoring device without requiring additional sensors, leads, or circuitry.

An implantable hemodynamic monitor may include a pressure sensor positioned along an intracardiac lead for measuring intracardiac pressure, for example right ventricular intracardiac pressure. An intracardiac pressure signal includes a respiration component caused by changes in intrathoracic pressure that occur during inspiration and expiration. The respiration component of a pressure signal is typically lower in frequency than the cardiac component. Methods and apparatus described herein allow a respiration signal to be derived from the intracardiac pressure signal. Accurate breath detection and various respiration parameters can be determined from the derived respiration signal.

FIG. 1 is a schematic diagram of a patient monitoring system including an implantable medical device (IMD) 10 coupled to a lead 14 positioned within a heart 8 in a patient's body 6. IMD 10 is at least capable of monitoring physiological signals and may or may not include therapy delivery capabilities. IMD 10 may correspond to a variety of implantable medical devices including a cardiac pacemaker, implantable cardioverter defibrillator, implantable hemodynamic monitor, a drug pump, a neurostimulator or the like. Accordingly, IMD 10 may be coupled to additional leads and/or catheters operatively positioned relative to the patient's heart 8 or other body tissues for deploying stimulating/sensing electrodes, other physiological sensors, and/or drug delivery ports. While lead 14 is shown terminated within the right ventricle of the patient's heart, it is recognized that lead 14 may be configured as a transvenous lead that extends into other heart chambers or blood vessels for positioning electrodes and/or physiological sensors in a desired location.

In one embodiment, IMD 10 corresponds to an implantable hemodynamic monitor capable of sensing and recording ECG signals and intracardiac pressure signals and storing cardiac electrical and hemodynamic data. ECG signals are sensed using one or more electrodes 18 carried by lead 14 or using alternative electrodes (not shown) incorporated on the hermetically-sealed housing 12 of IMD 10. Housing 12 encloses circuitry (not shown) included in IMD 10 for controlling and performing device functions and processing sensed signals.

Lead 14 is further provided with a pressure sensor 16. Pressure sensor 16 is used for monitoring pressure within the right ventricle. Pressure signals are monitored for determining metrics of hemodynamic function useful in monitoring heart failure status or diagnosing cardiac dysfunction. In embodiments described herein, the right ventricular intracardiac pressure signal obtained from sensor 16 is further used to derive a respiration signal. The respiration signal is processed for monitoring respiration and thereby provides additional useful data relating to the patient's condition. While heart failure monitoring is one application in which respiration monitoring can be useful, it is recognized that additional clinical applications will exist in which respiration monitoring using a pressure-derived respiration signal will be beneficial, one example being sleep apnea or other respiratory illnesses.

IMD 10 is capable of bidirectional communication with an external programmer 26 via telemetry link 28. Programmer 26 is used to program the operating mode and various operational parameters of IMD 10 as well as interrogate IMD 10 to retrieve data stored by IMD 10. Stored data may include data related to IMD function determined through automated self-diagnostic tests as well as physiological data acquired by IMD 10 using pressure sensor 16 and electrode(s) 18.

Programmer 26 is further shown in communication with a central database 24 via communication link 30, which may be a wireless or hardwired link. Programming data and interrogation data may be transmitted via link 30. Central database 24 may be a centralized computer or a web-based or other networked database used by a clinician for remote monitoring and management of patient 6. Various methods described herein and executed for deriving a respiration signal from a pressure signal, detecting breath cycles and deriving various respiration metrics may be implemented in one or more of the IMD system components shown in FIG. 1, namely in the IMD 10, programmer 26 and/or central database 24, and may include any combination of hardware, firmware and/or software. Programmer 26 may be embodied as a clinic-based programmer having full IMD programming and interrogation functionality or a home-based monitor having interrogation and perhaps limited programming functionality and used for remote patient monitoring. It is recognized that other external devices, such as other physiological monitoring devices or other types of programming devices, may be used in conjunction with IMD 10 and incorporate portions of the methods described herein.

Figure 2:
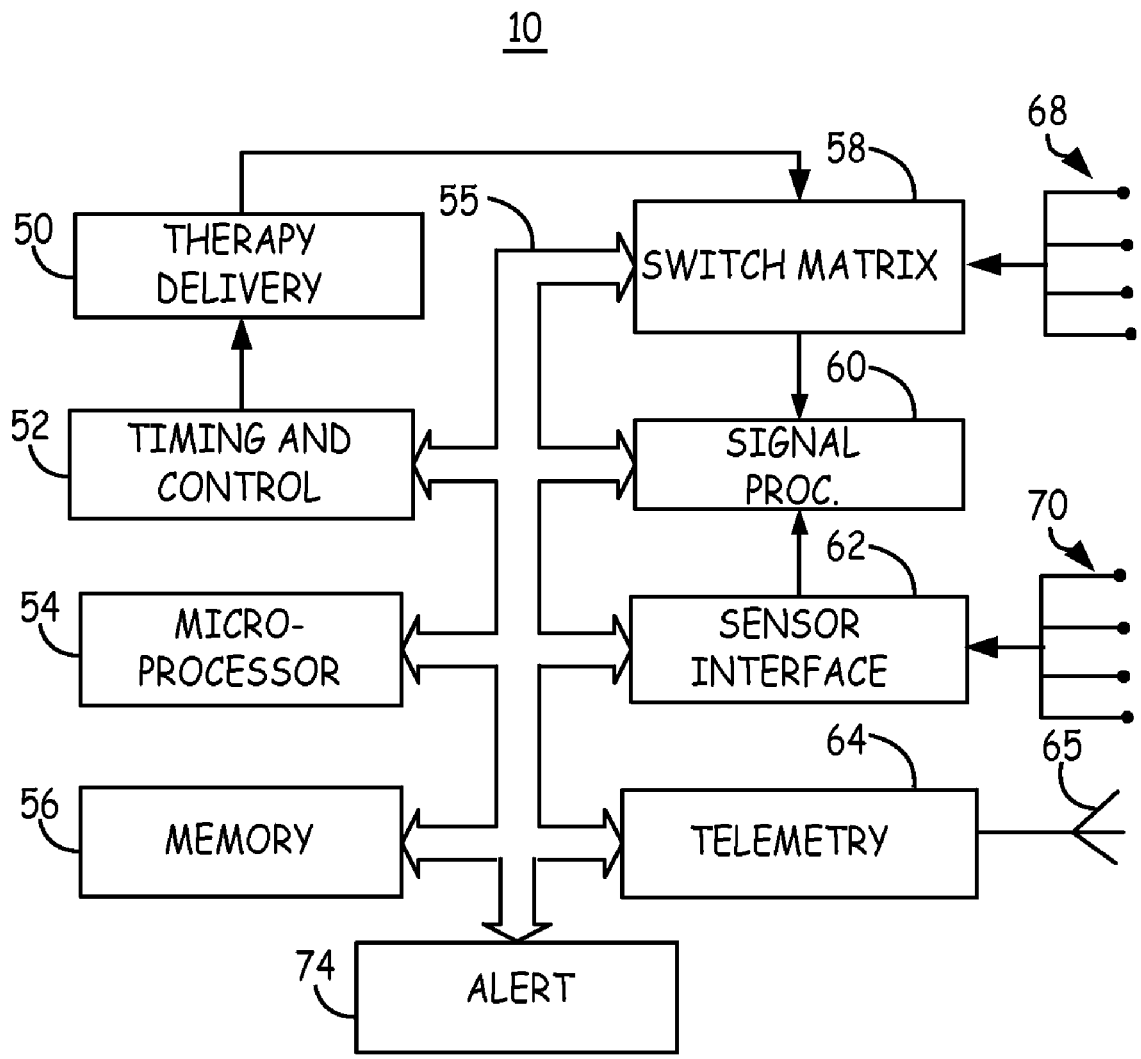
FIG. 2 is a functional block diagram of one embodiment of the IMD shown in FIG. 1.

FIG. 2 is a functional block diagram of one embodiment of IMD 10. IMD 10 generally includes timing and control circuitry 52 and an operating system that may employ microprocessor 54 or a digital state machine for timing sensing and therapy delivery functions (when present) in accordance with a programmed operating mode. Microprocessor 54 and associated memory 56 are coupled to the various components of IMD 10 via a data/address bus 55.

IMD 10 may include therapy delivery module 50 for delivering a therapy in response to determining a need for therapy, e.g., based on sensed physiological signals. Therapy delivery module 50 may provide drug delivery therapies or electrical stimulation therapies, such as cardiac pacing or anti-arrhythmia therapies. Therapies are delivered by module 50 under the control of timing and control circuitry 52. IMD 10 can be implemented as an interrupt-driven device in which case various computations, algorithms, or other device functions are executed upon generation of an interrupt signal.

Therapy delivery module 50 is typically coupled to two or more electrode terminals 68 via an optional switch matrix 58. Switch matrix 58 may be used for selecting which electrodes and corresponding polarities are used for delivering electrical stimulation pulses. Terminals 68 may be coupled to connectors providing electrical connection to electrodes incorporated in IMD housing 12 or other lead-based electrodes, including electrode(s) 18 carried by lead 14 (shown in FIG. 1).

Electrode terminals 68 are also used for receiving cardiac electrical signals through any unipolar or bipolar sensing configuration. Cardiac electrical signals may be monitored for use in diagnosing or managing a patient condition or may be used for determining when a therapy is needed and controlling the timing and delivery of the therapy. When used for sensing, electrode terminals 68 are coupled to signal processing circuitry 60 via switch matrix 58. Signal processor 60 includes sense amplifiers and may include other signal conditioning circuitry and an analog-to-digital converter. Electrical signals may then be used by microprocessor 54 for detecting physiological events, such as detecting and discriminating cardiac arrhythmias. As will be described herein, cardiac electrical signals received from terminals 68, which may be intracardiac EGM signals, far field EGM signals, or subcutaneous ECG signals, are used in one embodiment for determining a heart rate. The heart rate is used in performing heart rate dependent filtering of a pressure signal for deriving a respiration signal.

IMD 10 is additionally coupled to one or more sensors of physiological signals via sensor terminals 70. Physiological sensors include a pressure sensor 16 as shown in FIG. 1 and may further include accelerometers, flow sensors, blood chemistry sensors, activity sensors, postures sensors, or other physiological sensors known for use with implantable devices. Physiological sensors may be carried by leads extending from IMD 10 or incorporated in or on the IMD housing 12.

Signals received at sensor terminals 70 are received by a sensor interface 62 which provides sensor signals to signal processing circuitry 60. Sensor interface 62 receives the sensor signal and may provide initial amplification, filtering, rectification, or other signal conditioning. Sensor signals are used by microprocessor 54 for detecting physiological events or conditions. In particular, signals from pressure sensor 16 are processed by signal processor 60 and/or microprocessor 54 for deriving a respiration signal and determining respiration parameters therefrom. A respiration monitoring algorithm may be stored in memory 56 and executed by microprocessor 54 with input received from electrode terminals 68 and sensor terminals 70 for detecting respiration events. In one embodiment, microprocessor 54 is configured to execute software-implemented filtering operations for deriving a respiration signal from a sensed pressure signal and further perform processing of the derived signal for determining respiration metrics.

Microprocessor 54 is further configured to determine an adjustable threshold for detecting the onset of breath cycles and process the derived respiration signal using the automatically adjusted threshold for determining a breath rate. Additional algorithms may be implemented for determining other respiration parameters such as a respiratory effort metric or for detecting respiration-related events such as apnea, hyperpnea, hyopopnea, Cheyne-Stokes breathing, or other abnormal breathing patterns. The algorithms for executing the respiration signal derivation, breath rate determination, and other respiration parameter computations may be stored in memory 56 and retrieved therefrom by microprocessor 54 as needed.

In alternative embodiments, filtering operations for deriving a respiration signal as well as breath rate and other respiration parameter determination may be implemented using dedicated hardware and/or firmware implemented in signal processor 60. Signal processor 60 may include a filter for receiving the pressure signal from sensor interface 62. Signal processor 60 may be configured to digitize the input signal and filter the signal using a hardware-implemented heart-rate dependent filter for deriving a respiration signal. The signal processor may thus receive a heart rate input signal on bus 55 for filtering the pressure signal according to a determined heart rate. The heart rate is determined by microprocessor 54 using ECG/EGM signals received from electrode terminals 68. Signal processor 60 may then perform various threshold comparisons and peak detection operations as will be described herein for detecting breaths, determining a respiratory effort, or computing other respiration parameters.

Respiration data may be stored for use in diagnosing or monitoring the patient or for determining the need for delivering a therapy under control of the operating system. The operating system includes associated memory 56 for storing a variety of programmed-in operating modes and parameter values that are used by microprocessor 54. The memory 56 may also be used for storing data compiled from sensed physiological signals and/or relating to device operating history for telemetry out on receipt of a retrieval or interrogation instruction. Microprocessor 54 may respond to the respiration data by altering a therapy, triggering data storage, enabling other sensors for acquiring physiological data, or triggering alert 74 to generate an alert signal to the patient or a caregiver that a serious condition has been detected that may require medical intervention. Data relating to respiration may be stored in memory 56 for later retrieval.

IMD 10 further includes telemetry circuitry 64 and antenna 65. Programming commands or data are transmitted during uplink or downlink telemetry between IMD telemetry circuitry 64 and external telemetry circuitry included in a programmer or monitoring unit as shown in FIG. 1.

Figure 3:
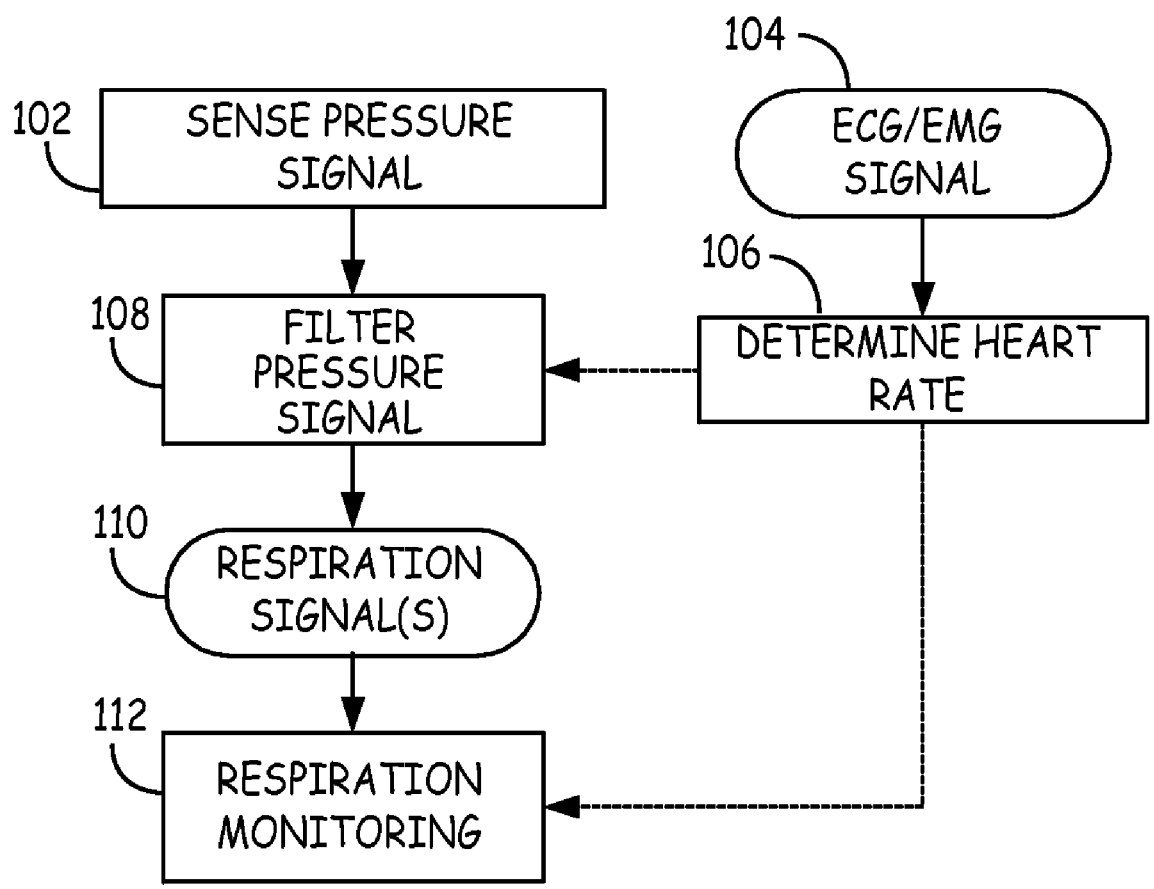
FIG. 3 is a flow chart of one method for monitoring respiration.

FIG. 3 is a flow chart of one embodiment of a method 100 for monitoring respiration using a pressure-derived respiration signal. Flow chart 100 and other flow charts presented herein are intended to illustrate the functional operation of a medical device system, and should not be construed as reflective of a specific form of software or hardware necessary to practice embodiments described herein. It is believed that the particular form of software, firmware and/or hardware will be determined primarily by the particular system architecture employed in the device system and by the particular detection and therapy delivery methodologies employed by the implantable device. Providing software, firmware and/or hardware to accomplish the operations described herein in the context of any modern implantable device system, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 102 a pressure signal is sensed using an implantable sensor. The sensed signal will include a cardiac component and respiration component and may include other noise and artifacts due to patient movement, coughing, sneezing, etc. The implantable sensor may be placed in a blood volume, for example in a heart chamber for measuring an intracardiac pressure signal or, alternatively, in a blood vessel. In one embodiment, the pressure sensor is positioned in the right ventricle for right ventricular intracardiac pressure sensing. Alternatively, the sensor may be placed in any anatomic location exposed to fluctuations in intrathoracic pressures associated with breathing, including, but not limited to, the pericardial space, mediastinal space, or intrapleural space. Pressure sensing at block 102 can be performed on a continuous or periodic basis.

The sensed pressure signal is filtered at block 108 using a heart rate dependent filtering frequency response. A filter used at block 108 may include a cascade of filters selected in various combinations to provide different filtering frequency responses, each corresponding to defined heart rate ranges. The heart rate dependent filter may alternatively include a bank of individual filters each having a unique frequency response selected individually for a particular heart rate range. Each filter provided for a given heart rate range may be a multistage filter, particularly when implemented in firmware or software. As described above, the heart rate dependent filter may be implemented in hardware, firmware or software. Thus, a heart rate dependent filter as described herein generally refers to a composite filter including at least two different single or multi-stage filter components or portions each having a unique frequency response corresponding to separately defined heart rate ranges.

The filtering performed at block 108 provides a derived respiration signal output as indicated at block 110, which may then be used as input for respiration monitoring algorithms at block 112. The respiration signal output provided at block 110 may include a single signal obtained by sequential operation of the different filter portions. In other words, the respiration signal is provided as a single continuous signal produced by merging the sequential output signals of the two different filter portions. The respiration signal output may alternatively include multiple filter output signals provided by each of the different heart rate dependent filter portions.

Respiration monitoring algorithms performed using a pressure-derived respiration signal will be described in greater detail below. Respiration monitoring performed at block 112 may be used for automatically controlling a therapy and/or recording respiration data for diagnostic or patient management purposes. In general, respiration monitoring at least includes detecting breath cycles to allow determination of a breath rate and may include determination of other respiration metrics.

At block 106, a heart rate is determined. The heart rate may be derived from the cardiac component of the pressure signal, for example using peak detection or threshold crossing algorithms for detecting each heart cycle length from the cardiac signal component. The quality of the cardiac signal component for use in determining a heart rate may be improved by performing high pass or band pass filtering of the pressure signal first. Alternatively, an ECG or EGM signal may be sensed as indicated by block 104 and used for determining a heart rate. For example, an EGM signal may be sensed using an intracardiac electrode or a subcutaneous ECG signal may be sensed using subcutaneously positioned electrodes for determining a heart rate. Heart rate determination from cardiac electrical signals is generally performed using R-wave detection algorithms and measuring R-R intervals.

The heart rate determined at block 106 is provided as input to the respiration monitoring algorithm 112 in one embodiment. When respiration data is computed from multiple heart rate dependent filter portions, respiration data is selected for storage in memory and data reporting purposes based on the determined heart rate. The respiration data selected is the data computed from a filter output signal obtained from the filter having a frequency response corresponding to the determined heart rate. The data obtained using filters having a frequency response designed for heart rate ranges not matching the determined heart rate may be discarded or archived.

Alternatively, the determined heart rate may be provided as input at block 108 for use in selecting which of the heart rate dependent filter portions is selected for filtering the pressure signal. The heart rate dependent filter portions may be selected one at a time according to the determined heart rate to generate a single respiration signal at block 110.

Figure 4:
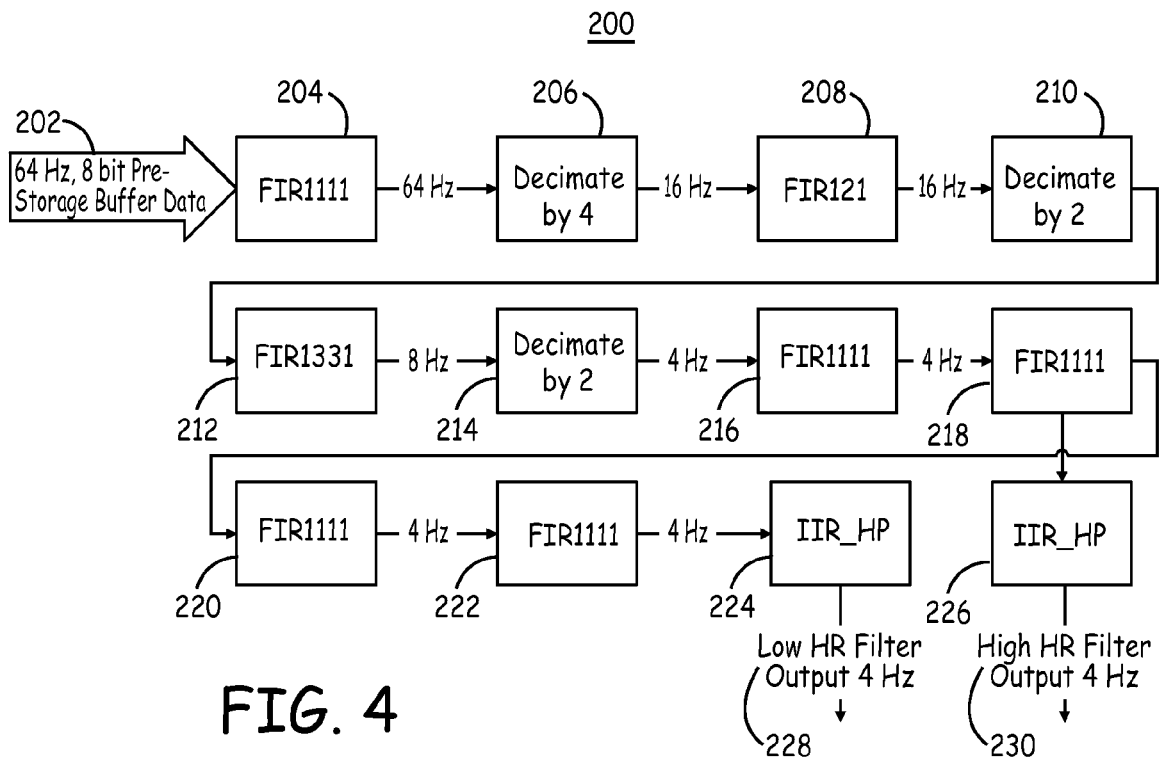
FIG. 4 is a block diagram of one embodiment of a multi-stage filter used for deriving a respiration signal from an intracardiac pressure signal.

FIG. 4 is a block diagram of one embodiment of a multistage filter 200 used for deriving a respiration signal from a pressure signal. A pressure signal, for example a right ventricular intracardiac pressure signal, is sampled at a desired sampling rate, which is suitable for the purposes of monitoring pressure and deriving cardiac function parameters. In the example shown in FIG. 4, the input signal 202 for filter 200 is a buffered 64 Hz, 8 bit signal. It is recognized that other pre-filter sampling rate and bit resolution signals may be utilized.

The composite filter 200 includes two heart rate-dependent multi-stage filter portions which are realized by selecting two different combinations of cascaded filter stages. The heart rate-dependent first filter portion is provided for filtering a respiration signal from the pressure signal during low heart rates, providing a low heart rate output 228. The first multistage filter portion includes filter stages 204, 208, 212, 216, 218, 220, 222 and 224.

The second heart rate-dependent filter portion is provided for deriving the respiration signal during high heart rates. The second filter portion is a computational subset of the low heart rate filter portion so that additional filter stages or computations are not required to implement the high heart rate filter portion. The second filter portion excludes filter stages 220 and 222 which were included in the low heart rate filter portion. The second filter portion thus includes filter stages 204, 208, 212, 216 and 218 and a final filtering stage 226, which may be equivalent to the final filtering stage 224 of the low heart rate filter portion. The second filter portion provides a high heart rate output 230.

In other embodiments, a single filter may be employed that is suitable for all heart rates or additional filter portions may be employed for finer heart rate resolution. The number of heart rate dependent filter portions included in the composite filter based on heart rate is not limited to two as shown in FIG. 4, i.e., one filter portion selected from the cascade of individual filter stages for a "high" heart rate range and another filter portion selected from the cascade of individual filter stages for a "low" heart rate range. The heart-rate dependent filter portions can include as many multi-stage or single stage filters as needed for a desired resolution of heart rate ranges, i.e., low, high, and one or more intermediate heart rate ranges.

Each portion of the multi-stage filter is designed to produce a desired overall filter frequency response in the time domain selectable according to heart rate. In one embodiment, a first filter is selected as one combination of the cascade of filter stages when the heart rate is equal to or less than 50 beats per minute. A second filter is selected as a different combination of the cascade of filter stages when the heart rate is greater than 50 beats per minute. The frequency response for each heart-rate dependent filter portion will be optimized according to the amplitude and frequency content of the respiratory and cardiac components contributing to the particular pressure signal being sensed.

In an illustrative embodiment, the first filtering stage 204 averages the most recent four signal samples, i.e. the x(i) through x(i−3) sample point amplitudes are summed, and the summation is divided by four:

$$y(i)=(x(i)+x(i-1)+x(i-2)+x(i-3))/4$$

The second filtering stage 208 averages the most recent signal sample, x(i), with twice the previous signal sample, 2*x(i−1), and the next previous signal sample (i−2):

$$y(i)=(x(i)+2*x(i-1)+x(i-2))/4$$

The third filtering stage 212 averages x(i), 3*x(i−1), 3*x(i−2) and x(i−3):

$$y(i)=(x(i)+3*x(i-1)+3*x(i-2)+x(i-3))/8$$

Stages 218, 220 and 222 can be implemented the same as the first stage 204, i.e., an average of the most recent four signal sample amplitudes. The final output stages 224 and 226 are implemented as:

$$y(i)=(15/16)*y(i-1)+x(i)-x(i-1)$$

While filter stages 224 and 226 are shown as the final stages in filter 200, it is recognized that filter stages 224 and 226 could alternatively be implemented earlier as a single stage included in both the high and low heart rate filters, for example prior to stage 216, to reduce redundancy.

The multi-stage filtering approach allows a computationally efficient software implementation of the desired heart rate dependent filtering responses. The particular embodiment shown is computationally efficient while allowing the resolution of the derived respiration signal to be maximized using the least number of bits. The heart-rate dependent filtering approach allows limited coefficient filters and lower sampling rates to be used, which reduces the computation required to implement a particular frequency response. The filter 204 reduces higher frequencies in the pressure signal, such that the signal may be decimated by 4. The next filter 208 then may operate on one-quarter of the samples to achieve further low-pass filtering that allows decimation by 2, and so on. The constants in the illustrative equations given above allow multiplications and divisions to be performed by shifts and adds. The particular order of the stages of the heart-rate dependent filters may be rearranged.

It is recognized that multiple heart rate-dependent filters may each be designed and implemented in hardware as a single stage filter having the final filtering response of the multistage filters implemented in software as shown in FIG. 4. It is further recognized that a hardware implemented filter may be implemented having a variable frequency response selectable based on a heart rate input. The filter frequency response characteristics are chosen based on the known relationships between heart rates and respiration rates.

In an interrupt-driven device, the heart rate dependent filters and a breath detection algorithm to be described herein are run upon every interrupt signal, e.g. on an interrupt signal generated every one second. A limited number of samples from the previous interrupt interval are saved to be used in the next interrupt interval to allow continuous filter processing of signal samples. For example, the last 3 sample points of a previous interrupt interval may be saved to be used as the x(i−1), x(i−2) and x(i−3) sample points in the filtering equations shown above with the first sample point x(i) taken from the current interrupt interval. In this way, continuous respiration monitoring can be performed as long as the pressure signal is available.

Between filter stages 204 and 208, 208 and 212, and 212 and 216 decimation is performed to reduce the sample number. The cascade of filtering and decimation shown in FIG. 4 allows the low heart rate and high heart rate filtering responses to be implemented within the computational bandwidth of a microprocessor included in an implantable medical device. In the particular example shown, decimation by 4 occurs at block 206. Decimation by 2 occurs at blocks 210 and 214. In the case of a 64 Hz input signal, both the low heart rate filter output 228 and the high heart rate filter output 230 is a 4 Hz signal.

Both of the low heart rate output 228 and the high heart rate output 230 are provided as input to a common algorithm for detecting respiration events. In other words, the respiration monitoring algorithm is implemented to operate on both outputs 228 and 230, simultaneously or sequentially.

Figure 5:
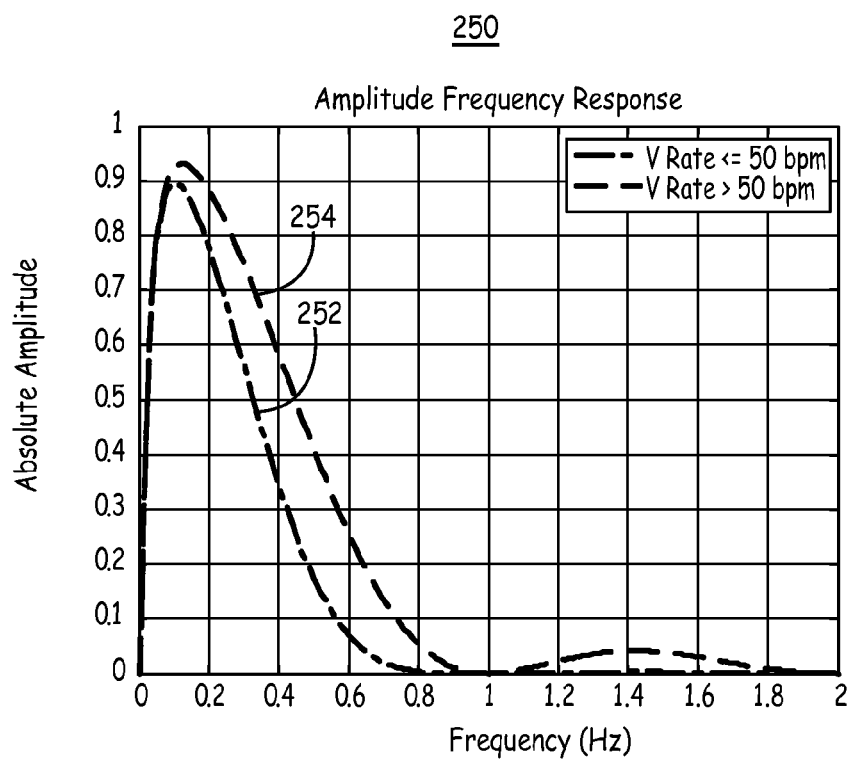
FIG. 5 is a plot of the amplitude frequency response for first, low heart rate filter portion and the second, high heart rate filter portion described in conjunction with FIG. 4.

FIG. 5 is a plot 250 of the amplitude frequency response for the first, low heart rate filter portion and the second, high heart rate filter portion described in conjunction with FIG. 4. The high heart rate filter frequency response 254 allows a higher frequency respiration signal to be derived from the intracardiac pressure signal. The low heart rate filter frequency response 252 reduces the likelihood of low frequency, cardiac-related pressure signals occurring at low heart rates from interfering with the derived respiration signal. Using the heart rate as input, the desired frequency response is selected and the pressure signal is filtered accordingly. While a composite filter having two selectable frequency responses for two different heart rate ranges is described herein, it is recognized that a heart rate dependent filter may include multiple filters or multiple selectable frequency responses, each of which may include multiple stages and selectable according to multiple heart rate ranges.

Figure 6:
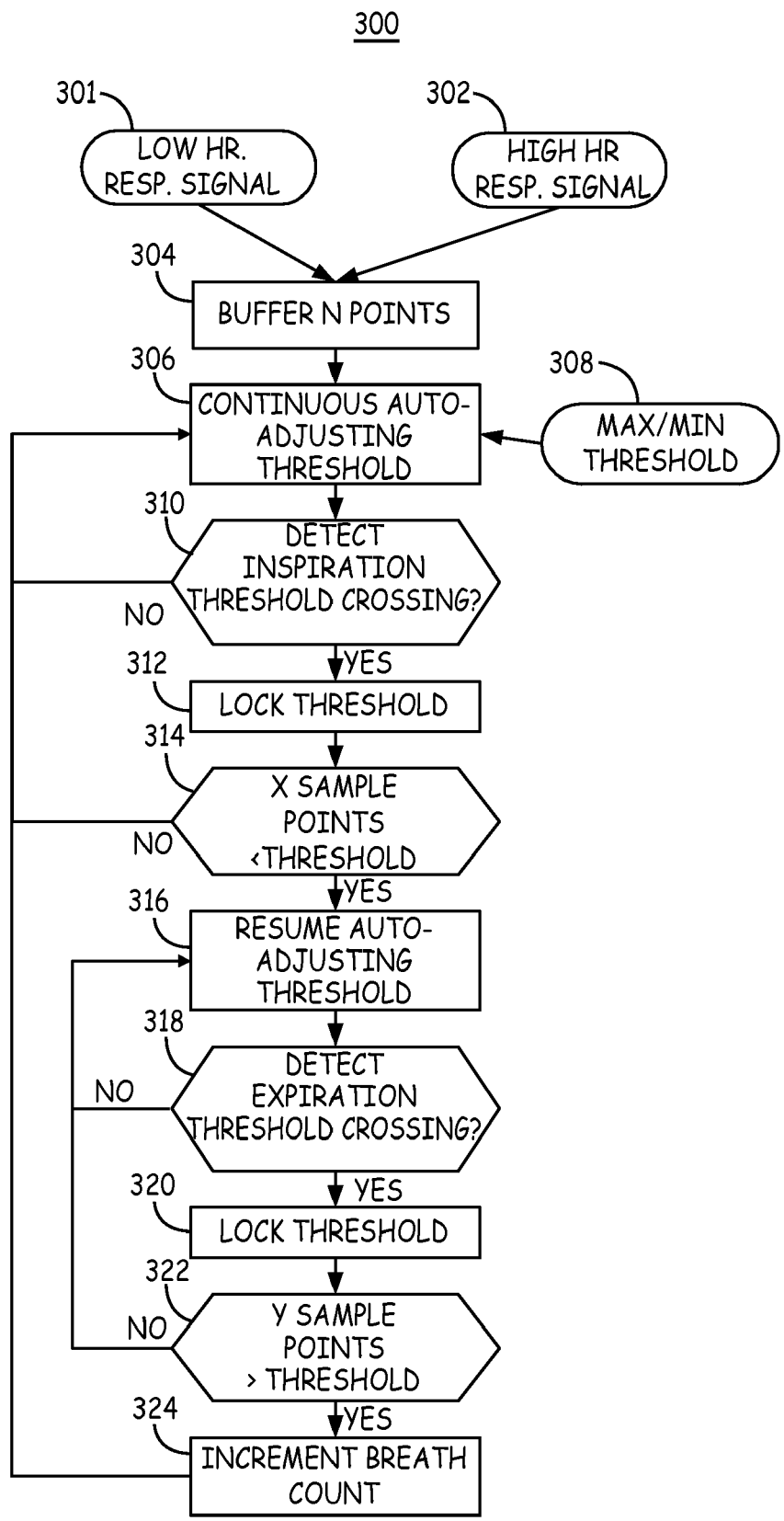
FIG. 6 is a flow chart of one method for detecting breaths using a respiration signal derived from a right ventricular intracardiac pressure signal.

FIG. 6 is a flow chart of one method 300 for detecting breaths using a respiration signal derived from a pressure signal, such as a right ventricular intracardiac pressure signal. Method 300 receives a pressure-derived respiration signal input for use in detecting breaths. At block 301, the pressure-derived respiration signal output from a low heart rate filter is provided as input to method 300. At block 302, the pressure-derived respiration signal output from a high heart rate filter is provided as input to method 300. Method 300 thus receives the signal output from each heart rate-dependent filter portion of a composite filter. The respiration signals in block 301 and 302 are derived using the heart rate-dependent, multi-stage filtering described in conjunction with FIG. 4.

In one embodiment, the filters may be configured to operate in a non-simultaneous, i.e. sequential, manner selected according to a presently determined heart rate. In this case, method 300 receives signal sample points from one heart rate-dependent filter portion at a time. The selected filter portion may be changing dynamically with heart rate changes, however a continuous digital signal will be received as input for the breath detection method 300 allowing continuous respiration signal monitoring. For example, upon an interrupt signal, the heart rate may be computed using the most recent cardiac sensed event(s). The heart rate is then used for selecting which filter portion is operating to filter the pressure signal until the next heart rate is determined. In alternative embodiments, a running average heart rate is updated upon each cardiac event, which may include sensed and paced cardiac beats when cardiac pacing is present. The heart rate may alternatively be an instantaneous heart rate based on a single event-to-event interval. The heart rate may be updated for each single event-to-event interval, such as each R-R interval, or every $i^{th}$ event interval or other selected intervals. The heart rate may alternatively be determined using several sensed and/or paced events and the corresponding time period over which the events occur. It is recognized that numerous methods for detecting an instantaneous or averaged heart rate may be used.

The determined heart rate may be used for prospective selection of the heart rate dependent filter portion. A selected filter may continue to operate for filtering the pressure signal until the next determined heart rate. Alternatively, the selected filter portion may operate until the heart rate has been in a different heart rate range for a predetermined period of time or predetermined number of sensed/paced events, thereby introducing a hysteresis effect in the selection of the filter portions.

In another embodiment, the rate-dependent filters operate in parallel each providing a pressure-derived respiration signal as input to method 300, to be processed simultaneously. In this case, breath cycles are detected and a breath count is determined according to method 300 for both the low HR respiration signal 301 and the high HR respiration signal 302. A final breath count for a given interval of time is then selected as the breath count determined from the filter output signal that corresponds to a heart rate determined at the end of the given interval of time. In operation, the breath count determined for the high heart rate filter signal is the default breath count value to be stored for data reporting purposes unless a heart rate below a threshold rate, for example 50 bpm, is detected, in which case the breath count determined using the low heart rate filter signal is stored for data reporting.

At block 304, a selected number of respiration signal sample points are continuously buffered in a first-in-first-out (FIFO) manner. If the filter output signals 301 and 302 are provided simultaneously for determination of a breath count for both the low HR filter signal count and the high HR filter signal, buffered sample points are collected for each signal in separate buffers for subsequent processing described below. If the filter output signals provided as input at 301 and 302 are provided sequentially according to a determined heart rate, buffered sample points may be stored from the sequential input signals in a single buffer for subsequent processing.

In one embodiment, ten sample points acquired from a 4 Hz filter output signal are stored in a memory buffer. Subsequent processing performed at blocks 306 through 324 is performed on both the low and high HR filter signals when both signals are provided in parallel or on the single, sequentially combined LR and HR filter signals provided during non-simultaneous, sequential operation of the low and high HR filters according to a determined heart rate.

The buffered sample points are used for continuously determining an automatically adjusted breath detection threshold at block 306. A dynamically adjusted threshold for detecting breaths is determined based on the varying amplitudes of the FIFO buffered sample points. The threshold is computed upon acquisition of each new sample point based on or as a function of the amplitudes of the buffered samples.

In various embodiments, the threshold may be computed as a threshold for detecting inspiration or a threshold for detecting expiration as the start of a breath cycle.

During inspiration, the intracardiac pressure signal is decreasing as intrathoracic pressure decreases. After high pass filtering, the inspiration phase of the filtered pressure signal can become negative in amplitude. The minimum peak of the pressure-derived respiration signal thus corresponds to the peak inspiratory effort. During expiration, intrathoracic pressure increases, and the respiration signal is generally positive in amplitude after highpass filtering of the pressure signal occurs. The maximum peak of the pressure-derived respiration signal corresponds to the peak expiratory effort.

A continuously adjusted breath-detection threshold may be based on either of a minimum or a maximum amplitude, i.e., a minimum or a maximum value, of the buffered sample points. In one embodiment, a new breath cycle is detected during inspiration. The onset of the new breath cycle corresponds to a sample point that is less than the automatically adjusted threshold. The auto-adjusted threshold is computed based on the minimum amplitude of the buffered sample points. The threshold may be computed as a percentage, for example between 30% and 40% of the minimum amplitude. In a test comparison of breath rates determined from actual respiration signals and from right ventricular pressure-derived respiration signals recorded in patients, an auto-adjusted threshold computed as 37.5% of the minimum amplitude of the buffered sample points was found to result in a high accuracy of breath detection.

Generally, the minimum amplitude of the derived respiration signal is a negative value such that the threshold computed as a percentage of the minimum amplitude will be a negative value having an absolute value less than the minimum amplitude. It should be noted that, in unusual circumstances, such as a patient on positive pressure ventilation, the pressure values may all be positive, but increasing and decreasing cyclically with the ventilator, with positive-going pressures associated with inspiration (forced by the ventilator) and negative-going pressures associated with expiration.

In some embodiments, a maximum and/or minimum limit may be set for the auto-adjusted threshold as indicated by input block 308. For example, a maximum threshold may be set which prevents the auto-adjusted threshold for detecting inspiration from ever exceeding the selected maximum. When computing the threshold as a percentage of the minimum sample point, the maximum threshold may be 0 or a small negative value, for example (−0.5) or (−1.0) depending on the relative amplitudes of the sample points.

Upon detecting a negative-going threshold crossing at block 310, i.e. a sample point having an amplitude that is less (more negative) than the auto-adjusted threshold, the continuous adjusting of the auto-adjusted threshold is temporarily suspended and the auto-adjusted threshold is locked at its current value at block 312. The FIFO buffer continues to receive new values but the threshold adjustment is suspended until a predetermined number of sample points (X) less than the current value of the auto-adjusted threshold are detected. In some embodiments, a predetermined number of consecutive sample points, e.g. 3 sample points, less than the threshold are required in order to confirm the detection of inspiration. If this requirement is not met at decision block 314, the method 300 returns to block 306 to continue adjusting the threshold and monitoring for the inspiration detection condition.

Once the inspiration detection requirement of X subthreshold sample points is satisfied at block 314, the automatic adjustment of the threshold is resumed at block 316. As such, the temporary locking of the threshold occurs for up to the predetermined number of consecutive subthreshold sample points required for inspiration confirmation. The threshold is then adjusted based on the current content of the buffer at block 316, which includes the subthreshold sample points used to confirm inspiration detection. After confirming inspiration, method 300 monitors for expiration by comparing sample points to the auto-adjusted threshold at block 318. An expiration threshold crossing is detected at block 318 when a positive-going crossing occurs, i.e. a sample point amplitude is equal to or greater than the auto-adjusted threshold. The sample point exceeding the threshold may be a positive value or a negative value.

In the embodiment illustrated by the flow chart of FIG. 6, the auto-adjusted threshold for detecting expiration continues to be computed at block 316 in the same manner as the auto-adjusted threshold for detecting inspiration computed at block 306, i.e., a percentage of the minimum sample point amplitude stored in the FIFO buffer. In alternative embodiments, the auto-adjusted threshold computed at block 316, after confirming inspiration detection at block 314, is computed differently than the inspiration detection threshold. For example, the expiration detection threshold may have a value that is based on a percentage of a maximum buffered sample point amplitude. In yet another embodiment, a percentage of the minimum buffered sample point amplitude used to compute the expiration threshold may be different than the percentage used to compute the inspiration threshold.

It is further recognized that computation of a single threshold or distinct inspiration and expiration thresholds may involve more than a single minimum or maximum buffered sample point. For example, an average or other statistical aspect of two or more buffered sample points may be used in computing the auto-adjusted threshold. When computing an auto-adjusted threshold for expiration detection, a minimum threshold value may be set to limit how low the threshold is set for detecting a positive-going threshold crossing.

In the example embodiment illustrated in FIG. 6, an expiration threshold crossing is detected at block 318 when a sample point that is greater than the auto-adjusted threshold is detected. The auto-adjusted threshold is again locked at its current value at block 320 to allow method 300 to confirm expiration detection at block 322. Expiration detection is confirmed by detecting a required number (Y) of consecutive sample points equaling or exceeding the locked threshold value (i.e., suprathreshold sample points). If a subthreshold sample point is detected before reaching the required number of consecutive suprathreshold sample points, method 300 returns to block 316 to continue automatic adjustment of the threshold and monitoring for expiration.

Once the required number of suprathreshold sample points is detected at block 322, breath detection is confirmed as evidenced by the confirmed detection of an expiration phase following an inspiration phase. A breath counter is incremented at block 324. Incorporating a required number of subthreshold sample points greater than one for confirming an inspiration threshold crossing (typically a negative-going crossing) helps to reduce the likelihood of false breath detections. The requirement of one or more suprathreshold sample points before detecting a breath based only on the inspiration detection introduces a form of hysteresis in the breath detection algorithm. This hysteresis reduces the likelihood of inappropriate breath detections due to noise, such as coughs, sneezes or sudden posture changes or other movement.

In FIG. 6, detection and confirmation of an inspiration phase of a breath cycle occurs at blocks 310 through 314 and is followed by detection and confirmation of a subsequent expiration phase of the breath cycle at blocks 316 through 322. Confirmation of each phase occurs before incrementing the breath count at block 324. Clearly the order of detecting and confirming the inspiration and expiration phases could be reversed from that shown in FIG. 6. In other words, blocks 318 through block 322 could be performed for detecting and confirming the expiration phase afterwhich blocks 310 through 314 are performed for detecting and confirming the inspiration phase before incrementing the breath count at block 324.

The practical number of required subthreshold and suprathreshold sample points for detecting a breath will be limited by the sampling rate. Requiring too many consecutive suprathreshold and subthreshold sampling points for confirming expiration and inspiration phases will limit the detectable breath rate and could result in underestimation of the breath rate. Generally, two suprathreshold sample points preceding (or following) an inspiration threshold crossing allows for accurate breath detection using a 4 Hz sampling rate of a pressure-derived respiration signal.

Figure 7:
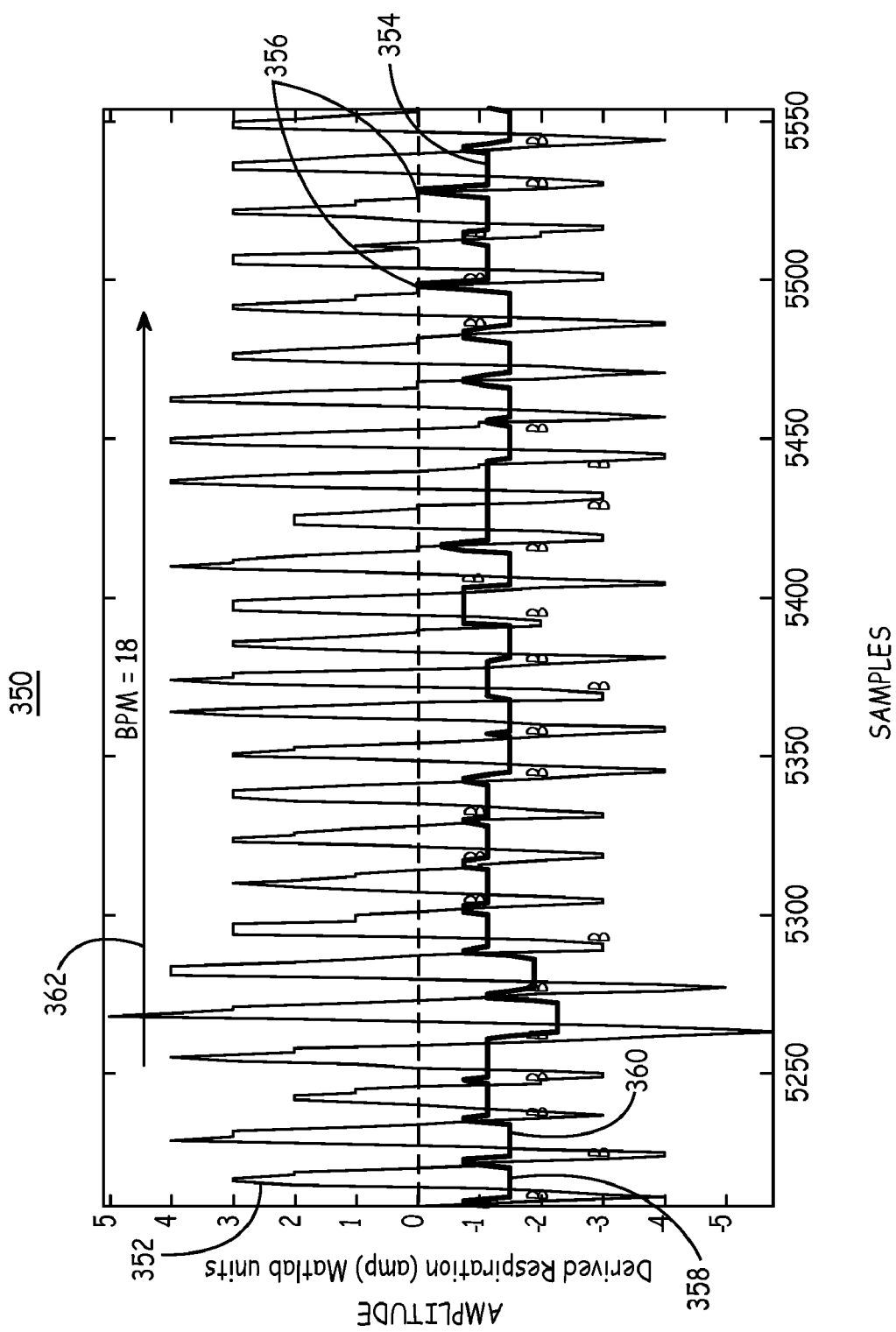
FIG. 7 is a plot of a pressure-derived respiration signal depicting the behavior of an automatically adjusted threshold for detecting breath cycles.

FIG. 7 is a plot 350 of a pressure-derived respiration signal 352 depicting the behavior of an automatically adjusted threshold 354 for detecting breath cycles. The auto-adjusted threshold 354, shown in heavy black line varies with the respiration signal 352. Plateaus, for example at 358 and 360 occur when the auto-adjusted threshold 354 is locked for confirming an inspiration phase or an expiration phase. Two occurrences of the auto-adjusted threshold reaching the maximum threshold limit (0 in this example) are seen at 356. Each breath is detected, as indicated by "B", upon a negative going threshold crossing that is preceded by a required number of subthreshold sample points which are further preceded by a required number of suprathreshold sample points. The number of breaths detected for a monitoring interval 362 are counted such that a number of breaths per minute (18 in this example) can be stored in device memory. The breath rate counted for repeating intervals 362 can be stored in memory to provide continuous breath rate monitoring. This respiration information can be utilized as an indicator of heart failure in the patient.

Figure 8:
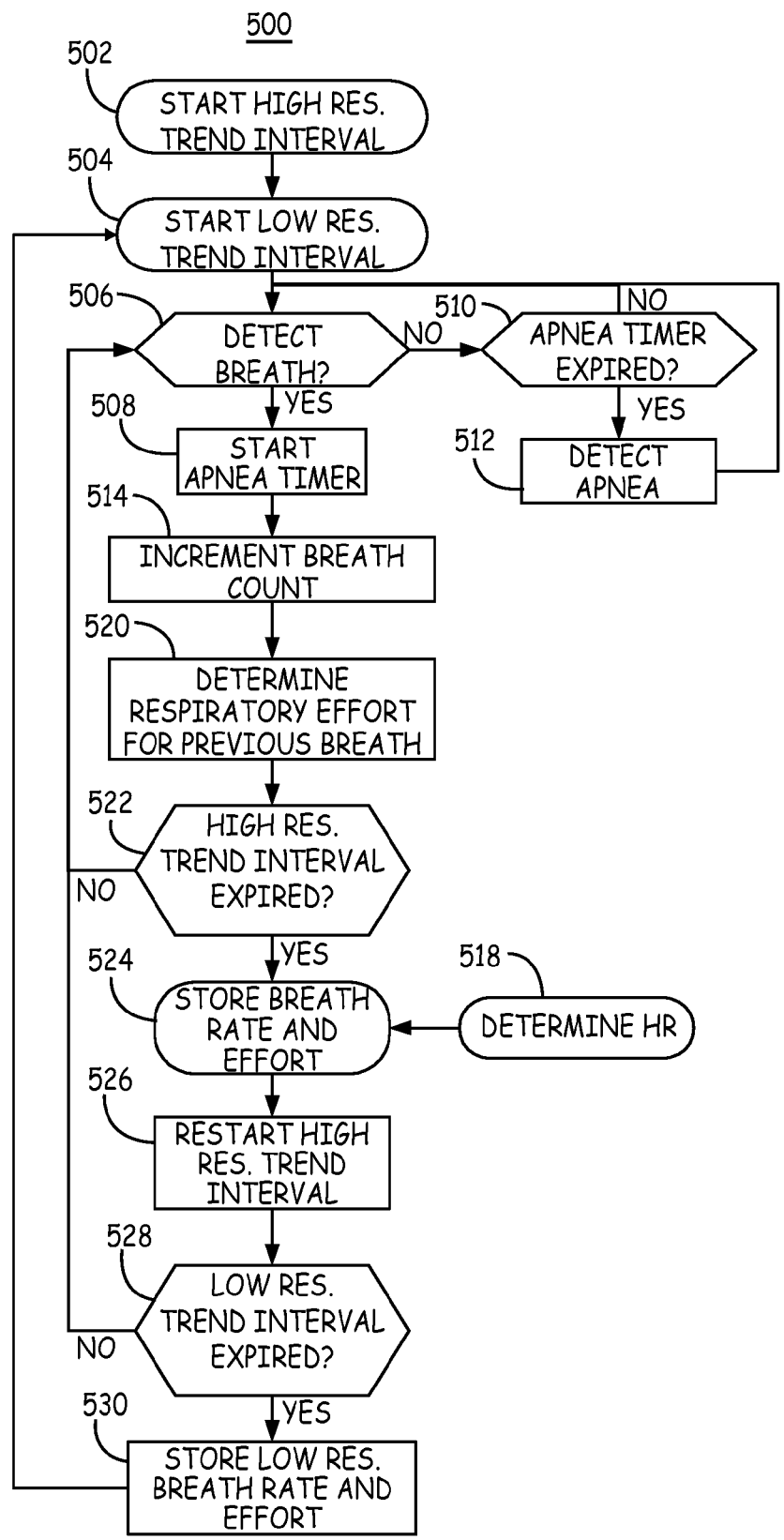
FIG. 8 is a flow chart of one method for monitoring respiration using a pressure-derived respiration signal.

FIG. 8 is a flow chart of one method 500 for monitoring respiration using a pressure-derived respiration signal. At block 502, a high resolution trend interval timer is started. At block 504, a low resolution trend interval timer is started. The resolution trend intervals may be programmable by a physician. Respiration data may be collected and stored over one or more repeating time intervals to provide varying resolutions of stored data. In one embodiment, a high resolution trend interval is approximately two seconds such that at least a respiration rate, i.e., the number of breaths detected in a two second interval, and optionally other respiration parameters, is stored at the end of every two second interval. Such data storage may occur periodically or continuously, twenty-four hours per day. A low resolution trend interval may be on the order of several minutes, hours or one day. In one embodiment, a low resolution trend interval is 8 minutes. The number of breaths per minute in a low resolution trend interval may be determined from the cumulatively stored high resolution trend data.

At block 506, a breath cycle onset is detected, using the method described in conjunction with FIG. 6. Upon the first breath detection, an apnea timer is started at block 508. If the apnea timer expires before the next breath detection, as indicated by block 510, apnea is detected at block 512. An apnea timer may be set to any desired time interval for detecting apnea. In one embodiment, the apnea timer is set at 10 seconds. Upon detecting apnea at block 512, a record of the apnea episode may be stored in memory. A therapy response may be provided or an alarm generated. After each subsequent breath detection, the apnea timer is restarted at block 508.

The breath count is increased by one at block 514 in response to the breath detection. A respiratory effort is determined at block 520 for the previously detected breath cycle, which has ended upon the current breath detection. One method for determining a respiratory effort is described below in conjunction with FIG. 9.

If the high resolution trend interval has expired, as determined at block 522, the breath rate and a metric of respiratory effort for the trend interval are stored at block 524. The high resolution trend interval is restarted at block 526. If breath counts have been determined for parallel, simultaneous heart rate dependent filter signals, the breath counts are temporarily stored for each filter signal. The heart rate is determined at the end of the high resolution trend interval at block 518. The heart rate may be determined based on R-R intervals measured during the high resolution trend interval or any other preceding time interval. In a composite filter including two heart rate dependent filters, if the heart rate is less than a rate threshold, such as 55 beats per minute, for example, the breath count and respiratory effort determined for a low HR filter signal are stored for data reporting purposes. If the heart rate is greater than the threshold, the breath count and the respiratory effort determined for the high HR filter signal are stored for data reporting purposes. Breath counts temporarily stored for the filter signal(s) that are not selected to be stored for data reporting purposes maybe discarded or archived. Alternatively, breath counts for both filters may be stored by the IMD until a heart rate determination is made at a future time, either by the IMD or by an external programmer or computer, at which time the appropriate breath rate data is utilized for reporting purposes.

If the low resolution trend interval has not yet expired, as determined at block 528, method 500 returns to block 506 to wait for the next breath detection. If the low resolution trend interval has expired, the low resolution breath rate and effort is stored at block 530. The low resolution breath rate and effort may be determined from the high resolution data cumulatively stored over the low resolution trend interval. The low resolution breath rate may be determined from a sum of the stored high resolution breath counts or an average breath rate determined using each of the stored high resolution breath rates stored over the low resolution trend interval. Alternatively, separate breath counters may be used for each trend interval to separately determine the high and low trend interval breath rates.

The breath rate may be stored and made available for display to a clinician in breaths per minute. Respiratory effort may be stored as an average of the effort computed for each breath cycle over the low resolution trend interval or as an average of the averages for each high resolution trend interval. After updating the low resolution data, method 500 returns to block 504 to restart the low resolution trend interval.

Figure 9:
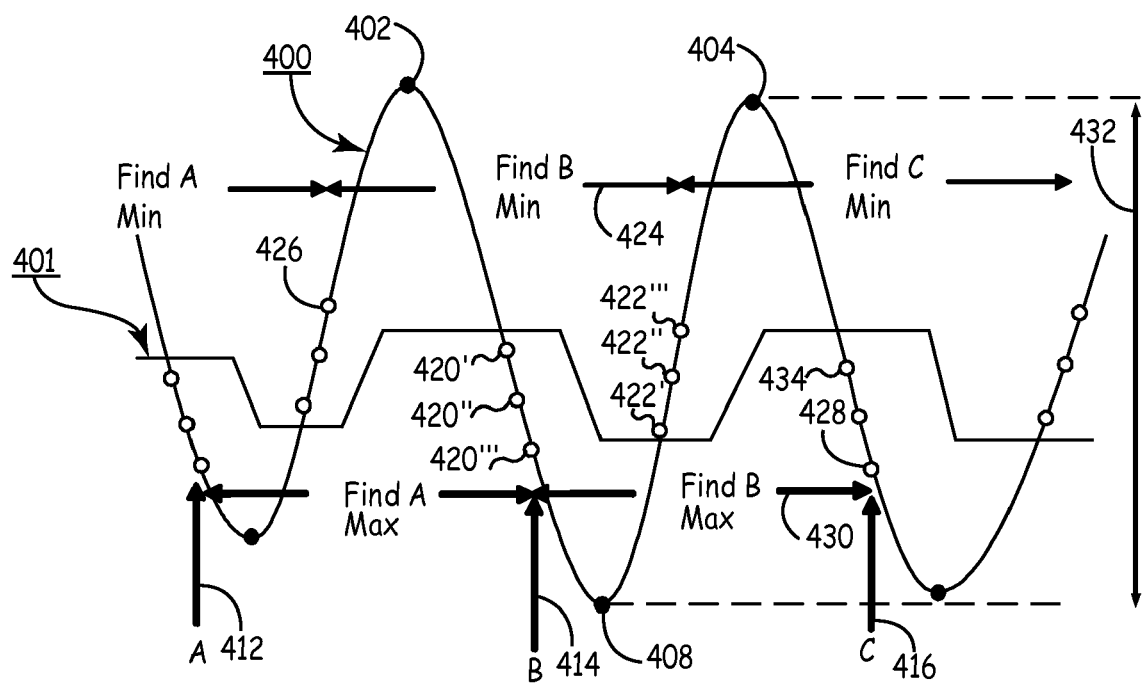
FIG. 9 is a plot of a respiration signal illustrating a method for computing a respiratory effort.

FIG. 9 is a plot of a respiration signal 400 illustrating methods for computing a respiratory effort. Long-term or continuous ambulatory monitoring of a measure of respiratory effort may be useful in detecting and assessing a respiratory parameter in heart failure patients, such as dyspnea, for example. The respiration signal 400 represents a pressure-derived respiration signal. An arbitrary auto-adjusting threshold 401 is illustrated. The detection of three breath cycles A, B and C is shown at 412, 414 and 416. Each breath detection 412, 414, and 416 occurs upon detecting the required number of subthreshold sample points preceded by a required number of suprathreshold sample points. Using breath cycle B detected at 414 as an example, a first subthreshold data point 420' is detected after which the threshold 401 remains locked to confirm the next two consecutive sample points 420" and 420''' are also subthreshold sample points. Upon detecting the third consecutive subthreshold sample point 420''', breath B is detected at 414. In other embodiments, a different number of subthreshold sample points may be required. The onset of the breath detection is shown to correspond to the last confirming subthreshold sample point in FIG. 9, however it is recognized that for timing and data extraction purposes, the onset of the breath cycle may correspond to any one of the subthreshold sample points 420', 420" or 420''', collectively referred to as 420.

Upon confirming the required number of subthreshold sample points 420 for inspiration detection, automatic adjustment of the threshold 401 resumes until a first suprathreshold sample point 422' is detected. The threshold 401 is again locked to allow confirmation of a required number of consecutive suprathreshold sample points 422" and 422'''. The confirmation of the suprathreshold sample points, collectively 422, is required before detection of the next breath C at 416 can occur.

Breath C 416 is detected upon confirming the required number of subthreshold sample points following the required suprathreshold sample points 422. Upon detection of breath C at 416, the respiratory effort 432 for the preceding breath B can be determined. In one embodiment, respiratory effort 432 is defined as the difference between the minimum amplitude 408 (peak inspiratory effort) and the maximum amplitude 404 (peak expiratory effort) of a breath cycle. The minimum amplitude 408 occurs during an inspiration phase of breath B. The minimum amplitude is searched for during a minimum peak search interval 424. Interval 424 is defined as the interval of time between the last suprathreshold sample point 426 used to confirm the expiration phase of breath A and the last suprathreshold sample point 422''' used to confirm the expiration phase of breath B. Interval 424 is thus inclusive of the inspiration phase of breath B (which occurs between peak expiratory effort 402 of breath A and peak inspiratory effort 408 of breath B). A minimum peak search is performed over interval 424 to reliably detect minimum peak 408 as the peak inspiratory effort of breath B detected at 414.

The maximum peak 404 of breath B is searched for during a maximum peak search interval 430. The search interval 430 extends from the last subthreshold sample point 420''' used to detect the onset of breath B at 414 to the last subthreshold sample point 428 used to detect the onset of breath C at 416. Interval 430 is thus seen to include the expiration phase of breath B, which extends between the peak inspiratory effort 408 to peak expiratory effort 404. A peak search performed over interval 430 will reliably identify peak 404 as the peak expiratory effort for breath B. The difference between maximum 404 and minimum 408 is computed as the respiratory effort 432 associated with breath B. It should be noted that the above described concept applies to a subject breathing normally, and that, in the case of a patient on a positive pressure ventilator, the respiratory effort measures will not have typical meaning, but rather, will be influenced by the ventilator settings.

Alternatively, the respiratory effort may be computed as the slope between maximum 404 and minimum 408. In other embodiments, a measure of respiratory effort may be computed as a slope between any selected sample point during the inspiration phase of a detected breath and a selected sample point during the expiration phase of the same detected breath.

The intervals for searching for the selected sample points used for computing a respiratory effort, such as intervals 424 and 430 may alternatively be defined using different sample points than those shown in FIG. 9. For example, an interval to search for a point during the inspiration phase for use in computing effort may be defined as the first subthreshold sample point 420' and the first suprathreshold sample point 422'. The interval to search for a point during the expiration phase for use in computing effort may be defined as the first suprathreshold point 422' and the subsequent first subthreshold point 434.

Thus, a system and method for respiration monitoring have been presented in the foregoing description with reference to specific embodiments. It is appreciated that various modifications to the referenced embodiments may be made without departing from the scope of the invention as set forth in the following claims.

We claim:

1. A method of determining a respiration parameter in a medical device, comprising:
   sensing a pressure signals to generate corresponding sample points;
   continuously adjusting a breath detection threshold in response to the generated sample points to generate a current adjusted breath detection threshold determined from the generated sample points;
   comparing a current generated sample point of the generated sample points to the current adjusted breath detection threshold;
   suspending the continuous adjusting of the breath detection threshold and setting the breath detection threshold equal to the most current adjusted breath detection threshold generated prior to the suspending;
   comparing a next sample point, generated subsequent to the suspending, to the set breath detection threshold; and
   determining the respiration parameter in response to the comparing of a next sample point to the set breath detection threshold.

2. The method of claim 1, wherein the continuously adjusting a breath detection threshold comprises:
   storing a predetermined number of generated sample points;
   setting the breath detection threshold equal to one of a minimum amplitude and a maximum amplitude of the current stored sample points; and
   updating the stored predetermined number of generated sample points to include a subsequently generated sample point.

3. The method of claim 1, further comprising determining whether both an inspiration detection threshold and an expiration detection threshold are sequentially detected in response to the comparing a next sample point.

4. The method of claim 1, wherein the respiration parameter is a breath count.

5. The method of claim 1, further comprising:
   confirming detection of an one of an inspiration and an expiration;
   resuming the continuous adjusting of the breath detection threshold;
   comparing a current sample point, generated subsequent to the resuming, to the current adjusted breath detection threshold;
   suspending the continuous adjusting of the breath detection threshold and setting the breath detection threshold equal to the most current adjusted breath detection threshold generated prior to the suspending;
   confirming detection of the other of an inspiration and an expiration; and
   incrementing a breath count in response to the confirming detection of the other of an inspiration and an expiration.

6. The method of claim 1, further comprising:
   determining a heart rate;
   filtering the sensed pressure signals in response to the determined heart rate to generate a heart-rate dependent frequency response; and
   deriving a filtered signal in response to the heart rate dependent frequency response, wherein the sample points are generated in response to the derived filtered signal.

7. The method of claim 6, wherein filtering the sensed pressure signals comprises filtering the sensed pressure signals using a first filter having a first frequency response corresponding to the determined heart rate being greater than a heart rate threshold and a second filter having a second frequency response different from the first frequency response, the second frequency response corresponding to the determined heart rate being less than the heart rate threshold.

8. The method of claim 7, wherein the first filter and the second filter are selected one at a time in a sequential manner in response to the determined heart rate and the filtered signal is obtained as a continuous signal comprising sequential outputs of the first filter and the second filter.

9. The method of claim 7, wherein filtering the sensed pressure signals comprises selecting the first filter and the second filter simultaneously for parallel filtering of the pressure signals, and wherein the filtered signal comprises a first signal component corresponding to an output of the first filter and a second signal component corresponding to an output of the second filter.

10. The method of claim 7, wherein the first and second filters each comprise multiple filtering stages, the first filter is a subset of the multiple stages of the second filter, and further comprising decimating the pressure signal following at least one of the multiple stages.

11. A method of determining a respiration parameter in a medical device, comprising:
    sensing a pressure signals to generate corresponding sample points;
    continuously adjusting a breath detection threshold in response to a minimum amplitude of a predetermined number of the generated sample points to generate a first detection threshold determined from the generated sample points;
    determining whether a current generated sample point of the generated sample points is less than the first inspiration detection threshold;
    suspending the continuous adjusting of the breath detection threshold and setting the first respiration detection threshold equal to the most current adjusted breath detection threshold generated prior to the suspending;
    determining whether a first predetermined number of next sample points, generated subsequent to the suspending, is less than the first respiration detection threshold;
    resuming the continuous adjusting of the breath detection threshold to continuously adjust the breath detection threshold in response to a maximum amplitude of the generated sample points to generate a second respiration detection threshold;
    determining whether a current generated sample point is greater than the second respiration detection threshold;
    suspending the continuous adjusting of the breath detection threshold and setting the expiration detection threshold equal to the most current adjusted breath detection threshold generated prior to the suspending;

determining whether a second predetermined number of next sample points, generated subsequent to the suspending, is greater than the second respiration detection threshold; and determining the respiration parameter in response to the predetermined number of next sample points being greater than the second respiration detection threshold.

12. The method of claim 11, wherein the first respiration detection threshold is generated using a first computation scheme and the second respiration detection threshold is generated using a second computation scheme different from the first computation scheme.

13. The method of claim 11, wherein the first predetermined number of next sample points is equal to the second predetermined number of next sample points.

14. The method of claim 11, wherein the respiration parameter is a breath count.

15. The method of claim 11, further comprising:
determining a heart rate;
filtering the sensed pressure signals in response to the determined heart rate to generate a heart-rate dependent frequency response; and
deriving a filtered signal in response to the heart rate dependent frequency response, wherein the sample points are generated in response to the derived filtered signal.

16. The method of claim 15, wherein filtering the sensed pressure signals comprises filtering the sensed pressure signals using a first filter having a first frequency response corresponding to the determined heart rate being greater than a heart rate threshold and a second filter having a second frequency response different from the first frequency response, the second frequency response corresponding to the determined heart rate being less than the heart rate threshold.

17. The method of claim 16, wherein the first filter and the second filter are selected one at a time in a sequential manner in response to the determined heart rate and the filtered signal is obtained as a continuous signal comprising sequential outputs of the first filter and the second filter.

18. The method of claim 16, wherein filtering the sensed pressure signals comprises selecting the first filter and the second filter simultaneously for parallel filtering of the pressure signals, and wherein the filtered signal comprises a first signal component corresponding to an output of the first filter and a second signal component corresponding to an output of the second filter.

19. The method of claim 16, wherein the first and second filters each comprise multiple filtering stages, the first filter is a subset of the multiple stages of the second filter, and further comprising decimating the pressure signal following at least one of the multiple stages.

* * * * *

UNITED STATES PATENT AND TRADEMARK OFFICE
CERTIFICATE OF CORRECTION

PATENT NO. : 8,372,013 B2
APPLICATION NO. : 12/262285
DATED : February 12, 2013
INVENTOR(S) : Maneesh A. Shrivastav Page 1 of 1

It is certified that error appears in the above-identified patent and that said Letters Patent is hereby corrected as shown below:

In the Claims:

Col. 17, line 22, delete the word "signals" and insert in place therefor -- signal --.

Signed and Sealed this
Thirtieth Day of July, 2013

Teresa Stanek Rea
*Acting Director of the United States Patent and Trademark Office*